United States Patent
Ragavan et al.

(10) Patent No.: US 6,294,188 B1
(45) Date of Patent: Sep. 25, 2001

(54) METHODS INVOLVING CHANGING THE CONSTITUTIVE AND STIMULATED SECRETIONS OF THE LOCAL REPRODUCTIVE SYSTEM OF WOMEN

(75) Inventors: Vanaja V. Ragavan, Wynnewood; Alan Laties, Philadelphia, both of PA (US)

(73) Assignee: Aviana BioPharm Inc., Wynnewood, PA (US)

(*) Notice: Subject to any disclaimer, the term of this patent is extended or adjusted under 35 U.S.C. 154(b) by 0 days.

(21) Appl. No.: 09/347,847

(22) Filed: Jul. 2, 1999

Related U.S. Application Data

(60) Provisional application No. 60/092,136, filed on Jul. 9, 1998.

(51) Int. Cl.$^7$ .............................. A61F 13/00; A61F 13/02; A61F 6/14; A61F 6/06; A61F 9/04
(52) U.S. Cl. ........................... 424/433; 424/45; 424/464; 424/489; 424/430; 424/431; 424/432; 424/434
(58) Field of Search .................................. 424/464, 489, 424/434, 430, 431, 432, 433, 45; 514/944, 945

(56) References Cited

U.S. PATENT DOCUMENTS

| | | |
|---|---|---|
| 4,139,638 | 2/1979 | Neri et al. |
| 4,264,582 | 4/1981 | Flora et al. |
| 4,344,941 | 8/1982 | Wiechert et al. |
| 4,456,600 | 6/1984 | Wiechert et al. |
| 4,501,729 | 2/1985 | Boucher et al. |
| 4,558,041 | 12/1985 | Wiechert et al. |
| 4,670,427 | 6/1987 | Annen et al. |
| 4,684,635 | 8/1987 | Orentreich et al. |
| 4,944,949 | 7/1990 | Story et al. |
| 5,093,133 | 3/1992 | Wisniewski et al. |
| 5,100,918 | 3/1992 | Sunshine et al. |
| 5,292,498 | 3/1994 | Boucher, Jr. |
| 5,294,433 | 3/1994 | Singer et al. |
| 5,344,651 | 9/1994 | Schwen et al. |
| 5,352,699 | 10/1994 | Jackson . |
| 5,364,885 | 11/1994 | Ahluwalia et al. |
| 5,369,126 | 11/1994 | Doran et al. |
| 5,541,172 | 7/1996 | Labrie et al. |
| 5,635,160 | 6/1997 | Stutts, III et al. |
| 5,654,337 | 8/1997 | Roentsch et al. |
| 5,719,197 | 2/1998 | Kanios et al. |
| 5,777,134 | 7/1998 | Bakshi et al. |
| 5,811,111 | 9/1998 | McAtee et al. |
| 5,837,289 | 11/1998 | Grasela et al. |
| 5,853,751 | 12/1998 | Masiz . |
| 5,854,230 | 12/1998 | Tannabe et al. |
| 5,863,560 | 1/1999 | Osborne . |
| 5,874,095 | 2/1999 | Deckner et al. |
| 5,879,701 | 3/1999 | Audett et al. |
| 5,885,597 | 3/1999 | Botknecht et al. |
| 5,888,523 | 3/1999 | Galask et al. |
| 6,015,806 | 1/2000 | Labrie et al. |

FOREIGN PATENT DOCUMENTS 0 159 012 A2  10/1985  (EP) .

OTHER PUBLICATIONS

Audie, et al., "Expression of human mucin genes in respiratory, digestive, and reproductive tracts ascertained by in situ hybridization," *J. Histochem. Cytochem.* 41(10):1479–85 (1993).

Audie, et al., "Mucin gene expression in the human endocervix," *Hum. Reprod.* 10(1):98–102 (1995).

Chretien, "Ultrastructure and variations of human cervical mucus during pregnancy and the menopause," *Acta Obstet. Gynecol. Scand.* 57(4):337–48 (1978).

Dunson, et al., "Timing of oneset of contraceptive effectiveness in Norplant implant users. Part I. Changes in cervical mucus," *Fertil. Steril.* 69(2):258–66 (1998).

Fordney–Settlage, "A review of cervical mucus and sperm interactions in humans," *Int. J. Fertil.* 26(3):161–9 (1981).

Gipson, et al., "Mucin genes expressed by human female reproductive tract epithelia," *Biol. Reprod.* 56(4):999–1011 (1997).

Gorodeski & Hopfer, "Regulation of the paracellular permeability of cultured human cervical epithelium by a nucleotide receptor,"*J. Soc. Gynecol. Investig.* 2(5):716–20 (1995).

Katz, "Human cervical mucus: research update," *Am. J. Obstet. Gynecol.* 165(6 Pt 2):1984–6 (1991).

Kopito, et al., "Water and electrolytes in human cervical mucus," *Fertil. Steril.* 24(7):499–506 (1973).

Moghissi, "The function of the cervix in fertility," *Fertil. Steril.* 23(4):295–306 (1972).

Petta, et al., "Timing of onset of contraceptive effectiveness in Depo–Provera users: Part I. Changes in cervical mucus," *Fertil. Steril.* 69(2):252–7 (1998).

Slomiany, et al., "Enhancement in the protective qualities of gastic mucus by ebrotidine during duodenal ulcer healing," *Gen. Pharmacol.* 26(5):1039–44 (1995).

Slomiany, et al., "Gastroprotective properties of ebrotidine. A review," *Arzneimittelforschung.* 47(4A):459–67 (1997).

Primary Examiner—Thurman K. Page
Assistant Examiner—Amy E Pulliam
(74) Attorney, Agent, or Firm—Holland & Knight LLP

(57) ABSTRACT

The first aspect of the invention relates to a method of inducing changes in the cervical mucus of a person to achieve a contraceptive effect, and wherein the method involves administering to the person an effective amount of ebrotidine sufficient to achieve a contraceptive effect. The second aspect of the invention involves a method for treating atrophic vaginitis urinary incontinence and their associated signs and symptoms, in a person, the method involves administering to the person an effective mount of an agent sufficient to treatment of atrophic vaginitis, the agent being selected from a group consisting of stimulants or antagonists, purinergic receptors, a sodium ion update agents and an anion secretion inhibitors.

16 Claims, No Drawings

METHODS INVOLVING CHANGING THE CONSTITUTIVE AND STIMULATED SECRETIONS OF THE LOCAL REPRODUCTIVE SYSTEM OF WOMEN

This appln claims the benefit of Provisional No. 60/092,136 filed Jul. 9, 1998.

1. General Concepts of the Invention

This invention covers novel methods of treating several conditions of women by changing the constitutive and stimulated secretions of the local reproductive system including the uterine, uterine cervix, fallopian tubular secretions and vaginal secretions, secretions of the Bartholin or vestibular glands and urethral secretions. This invention also covers agents which can influence the function of the mucus genes found in the reproductive system, including, but not limited to the cervix, uterus, and Bartholin's glands and other parts of the reproductive system with mucus secreting cells. Both squamous epithelium of the lower genital tract (vagina; for example) and epithelial cells of the upper reproductive tract (the various parts of the uterus, for example) are included in this invention. Included are methods to influence or change the secretary effects of the mucus genes and mucus secreting cells and cells that influence the properties of secretory and cell surface mucins of all the above mentioned glands of the reproductive system. Changing the hydration, viscosity or other properties or stimulating the secretions can have potential uses in a variety of conditions and disorders, including, but not limited to contraception, infertility, menopause, dyspareunia, infections, and others related and unrelated conditions. Description of the function and anatomy of these organs can be found in Novak's Gynecology, 12th edition, eds. Berek, Adashi and Hillard, Williams and Wilkins, Baltimore, Md., 1996.

Although steroidal actions on the reproductive system are well known, this invention will in particular, discuss the development of non-steroidal factors that may control the reproductive system. These products could potentially act on the cells of the reproductive system to augment steroid action or act in the absence of steroid action, as the case may be. Some of the approaches proposed in the invention are derived from research conducted on the actions of mucin genes and other cell systems in non-reproductive arenas. The invention will apply these new discoveries to the reproductive system to develop a new series of non-steroidal products targeted toward condition of the female reproductive system such as atrophic vaginitis and could also function as a contraceptive.

There are two aspects to this invention. The first concept is the use of an agent or agents to increase the viscosity and nature of mucus of the reproductive organs, with such an action being utilized as a potential contraceptive. A specific agent, ebrotidine, is described in more detail later. The second concept is the use of agents to increase the amount and/or the water content of secretions of the reproductive organs including mucus and transudative secretions. Specifically, agents described in this invention include purinergic agents that are known to increase water content of secretions in systems such as the lung. This concept will be used for the invention to generally increase the lubrication of the reproductive system.

In particular, we describe several methods which could potentially change the quantity and quality of the secretions of the reproductive organs and influence mucosal gene and mucosal cell actions. Some influences on mucus secretion include, but not limited to content of mucin elements such as sulfo and sialomucins, changes in viscosity, hydrogen ion retardation, hydrophobicity, changes in phospholipid content, glycosylation and sulfation, macromolecular assembly. Also included are potential changes in growth factors such as, but not limited to tumor necrosis factor alpha and epidermal and platelet derived growth factors, effect on agents such as integrins, and other agents of the inflammatory and healing processes and agents that influence proteinases and other agents related to mucin breakdown. Influences of the covered agents on mucus properties such as but not limited to surface tension and adhesivity, transport properties and Theological properties such as but not limited to viscosity, elastic modulus, tensile properties, rigidity factors, recoil factors, spinnbarkeit, sperm penetration qualities, consistency, cellularity, ferning, etc. are also included in this patent. A variety of products, which can influence the mucosal gene and/or mucosal epithelium in the presence or absence of estrogens, progestogens, their natural and synthetic derivatives and other sex steroid hormones are described.

2. Secretory Functions of Endothelium and Epithelium of the Reproductive Glands and Their Physiology and Pathology Secretory functions of the uterine cervical mucous secreting cells and vaginal mucosal cells have profound impact on the function of the reproductive tract. Cervical mucus changes in quality and quantity throughout the menstrual cycle. Under the influence of rising estrogen levels, cervical mucus becomes thin, allows the passage of spermatazoa and has a characteristic quality called spinnbarkeit—it can be stretched into a thin, adhesive strand. Under the influence of progesterone later in the menstrual cycle, the mucus becomes thick and hostile to sperm penetration, closing the window of fertility. In fact, thickening of cervical mucus is thought to be one of the primary modes of contraceptive action for progestin-only contraceptives.

After menopause, cervical mucus becomes scant and highly viscous, contributing to vaginal dryness and lack of lubrication. Stimulation of cervical mucus production at this time, along with changes in vaginal mucosa should help alleviate vaginal dryness, and can also augment the action of exogenously administered estrogen's effect on this condition.

3. Mucin Gene Expression in the Uterine Cervix

Extensive investigation has revealed that cervical epithelia express at least five of the many known mucin genes. For instance, the epithelium of the mucosal surface of the endocervix expresses genes designated as MUC 1;4;5AC;5B and 6 while the vaginal epithelium expresses MUC 1 and 4.[1] Another study showed that MUC 4 was most intensely expressed using in-situ hybridization, conducted predominantly during the luteal phase. The expression of this particular gene appears to be dependent partly on the estrogen/progesterone ratio.[2] Of particular relevance to this invention, the same investigators have shown that MUC 4 and 5B are also expressed in the gastric mucosa.[3]

[1.] Gipson I K, Ho S B, et al. Mucin Genes expressed by human female reproductive tract epithelia. Bio. Reprod. 1997:56:999–1011.
[2.] Audie J P, Tetaert D. et al. Mucin gene expression in the human endocervix. Hum Reprod. 1995:10:98–102.
[3.] Audie J P et al. Expression of Human Mucin Genes in Respiratory, Digestive, and Reproductive Tracts ascentrained by in-situ hybridization. J. Histochemistry and Cytochemistry. 1993:41:1479–1485.

4. The Uterine Cervix, Hormonal Influences and its Role in Reproduction

As an active gatekeeper to the internal reproductive organs, the uterine cervix of a person plays a critical role in reproduction. As Katz outlines in his review,[4] the following functions can be attributed to the cervical mucus and its role in reproduction: 1) Semen is filtered at the cervical os and sperm allowed entry into the uterus from a relatively hostile vaginal environment; 2) Sperm are nurtured within the cervical canal and supported and prepared for capacitation; 3) Sperm are stored and later released in order to co-ordinate with ovulation.

[4.] Katz, D. F. Human Cervical Mucous: Research Update. Am. J. Obstet. Gynecol. 1991:165:1984–6.

Under the influence of estrogen, cervical mucus becomes thin and much less viscous, with a ferning pattern seen when spread on a slide.[4] The actual mechanism whereby estrogen changes the cervical mucus is not clearly understood, but Nicosia, in his review, outlines key concepts.[5] Cervical mucus is a mixture of mucin secreted by the mucus cells and transudation of capillary exudates, which include water (85–98%), electrolytes, serum and locally derived proteins. The mucins are responsible for the rheological properties of mucus, but comprise less than 1% in volume. Apparently, during the mid-cycle, estrogens stimulate the stromal cells, which in turn stimulate the mucus cells. The mucus produced during this time has a higher water content, accounting for part of the rheological changes such as ferning.

[4.] Katz, D. F. Human Cervical Mucous: Research Update. Am. J. Obstet. Gynecol. 1991:165:1984–6.
[5.] Nicosia S V. Physiology of the Cervical Mucus. Sem. In Reproductive Endocrinology. 1986;4:313–321.

Under the influence of estrogen, the human cervix secretes a profuse, clear and thin mucus, and about 600 mg of mucus a day, in the pre-ovulatory and ovulatory phases of the menstrual cycle. Under the influence of progestins, this decreases to 20–60 mg/day and the mucus is thick and viscous.[6]

[6.] Moghissi, K S. The function of the cervix infertility. Fert. Steril. 1972 23:295–306.

The viscosity of cervical mucus changes in a parallel fashion with externally administered progestins given as contraceptive products. For instance, Norplant, a levonorgestrel containing implant, changes the cervical mucus within 3 days of insertion and this action is considered one of the critical factors responsible for its contraceptive action.[7] A similar finding was shown with another progestin only product—Depo-Provera.[8] Clearly, changes in cervical mucus could have a contraceptive effect because the secretion of progesterone is associated with a considerable decrease in fecundity and a closing of the window of fertility.

[7.] Dunson T R et al. Timing on onset of contraceptive effectiveness in Norplant implant users. Part I. Changes in cervical mucus. Fert. Steril. 1998:69:258–66.
[8.] Petta C A et al. Timing of onset of contraceptive effectiveness in Depo-Provera users: Part I. Changes in cervical mucus. Fertil Steril. 1998:69:252–7.

5. Changes in the Secretory Functions of the Cervix and Vagina During Menopause As estrogen levels fall in the menopause, estrogen dependEnt tissue will start to involute and take on the characteristic appearance of estrogen deprivation. In particular, human cervical mucus becomes scanty. In vitro, this mucus has been shown to be impenetrable to sperm.[9]

[9.] Chretien F C. Ultrastructure and variations of human cervical mucus during pregnancy and the menopause. Acta. Obstet. Gynecol. Scand. 1978 57:337–348.

The vaginal mucosa also regresses during menopause. With aging, the vagina becomes shortened, ruggae disappear, and elasticity is lost. Vaginal secretion becomes scanty. When estrogen is provided, some of these effects are reversed: the cervix starts to secrete some mucus and the vaginal mucosa regains its lost layers, but often the symptoms do not disappear completely partly because the amount of estrogen provided for hormone replacement is lower than circulating estrogen levels during a normal menstrual cycle.

6. Cervical Mucus: its Rheological Properties and Role in Reproduction

As mentioned previously, the composition of the cervical mucus changes under hormonal influence. Estrogen stimulates the production of thin, isotonic mucus, with increased amounts of high molecular weight glycoproteins. Progesterone produces relatively viscous mucus. Cervical mucus contains 98% water at mid cycle and 90% at other times.[10] Cervical mucus is also rich in metallic ions, enzymes (such as alkaline phosphatase, etc.), soluble proteins and salts.[11] The gel phase of cervical mucus contains primarily a form of mucin, a high molecular weight glycoprotein. Mucin micelles cross-link by disulfide bridges. Estrogen and progestogens control the arrangement of these micelles.[11] These micellar arrangements influence the rheological properties of mucus.

[10.] Kopito L et al. Water and electrolytes in human cervical mucus. Fertil. Steril. 1973;24:499–506.
[11.] Fordney-Settlage, D. A review of cervical mucus and sperm interactions in humans. Int. J. Fertil. 1981;26:161–169.

The evaluation of mucus and its properties are defined by chemical, physical and biological properties. Rheological or flow properties of mucus include viscosity, rate of flow, shear index, spinnbarkeit or stretch of mucus due to increased viscoelasticity and ferning (crystallization) parameters.

7. Ebrotidine for Use as a Contraceptive

Systemic contraceptives such as oral contraceptives and implants have many side effects, which can result in poor compliance or lack of usage. For instance, irregular bleeding and weight gain are some of the minor side effects, while major side effects such as venous and pulmonary thromboembomobolism are also found. Local contraceptives such as diaphragms are not as effective. These problems lead to poor compliance or to lack of use altogether, as evidenced by the large number of unintended pregnancies in spite of the availability of many types of contraceptives. There is a great need for innovative and safe new contraceptive products.

The focus of this aspect of this invention is in the area of contraception is to develop a safe, non-steroidal, locally active product that will change the nature of cervical mucus, rendering it hostile to sperm penetration. The aspect of the invention could potentially develop as a product that will not dynamically disturb the woman's reproductive system, but will provide contraceptive efficacy. It is anticipated that the drug may be given either locally or systemically.

Ebrotidine—a New Agent with Mucospissic Qualities

This invention pertains to a novel use of the known influence of a new drug, ebrotidine, (benzene sulfonamide N-[[[2-[[[2-[(aminoiminomethyl)amino]-4-thiazolylmethyl0thio]ethyl]amino]methylene]-4-bromo [CAS]) [CAS-100981-43-9] a H2 receptor blocker with profound effect on gastric mucus, as a potential contraceptive. This product is being developed for gastric ulcer healing, as described in EP Patent Number 159012, priority date ES8404418. A use other than gastric ulcer healing for this product has been filed, as noted in U.S. Pat. No. 5,294,433, in which this product is used for gingivitis. Ebrotidine is currently marketed in Spain for the treatment of gastric ulcer and is under clinical investigation in the rest of Europe.

Of particular interest to this aspect of the invention are ebrotidine's unique actions on the functionality of gastric mucosa as shown below. It is known that the mucous secretion of the gastric mucous cells parallels in several respects (mucus genes post-translational processing) that of the cervical mucus cell of the reproductive system. The invention involves the use of ebrotidine to influence the mucous secretion of the cervix, thereby rendering the mucous thick and viscous and hostile to sperm and acting as a potential contraceptive in pre-menopausal women. A more viscous mucus is already known to have contraceptive effects since progesterone and progestins change the cervical mucous secretion to a viscous, thick secretion either during the luteal phase of the menstrual cycle or during the intake of progestin containing products used for contraception, such as Norplant™.

In clinical studies involving gastric ulcers, the product has evaluated for a time period of few weeks. Accordingly, in accordance with the present invention, it is believed that ebrotidine may be successful as a non-steroidal locally acting product for contraception. A recent publication has reviewed ebrotidine's gastric and biochemical properties.[12]

[12.] Slomiany, B L, Piotrowski, J and Slomiany, A. Gastroprotective Properties of Ebrotidine. A review. Arzneim-Forsch/Drug Research 1997. 47:459–467.

Ebrotidine has been extensively studied in experimental animal models evaluating its effect on gastric mucus.[12, 13] Moreover, a complete package of preclinical toxicology studies has been conducted, including acute and chronic toxicology, reproductive, genotoxicity, reproductive toxicity, and carcinogenicity studies conducted up to 24 months of exposure. Overall, no serious adverse effects were seen with ebrotidine in these pre-clinical studies. Specifically, no effects were found on reproductive or genotoxicity screens and no hyperplastic and/or dysplastic changes were seen in carcinogenicity studies.

[12.] Slomiany, B L, Piotrowski, J and Slomiany, A. Gastroprotective Properties of Ebrotidine. A review. Arzneim-Forsch/Drug Research 1997. 47:459–467.
[13.] Slomiany, B L et al. Enhancement in the protective quality of gastric mucus by ebrotidine during duodenal ulcer healing. Gen. Pharmacol. 1995, 26: 1039–1044.

More than 500 patients with gastric ulcers have been treated with ebrotidine, with drug exposures up to 8 weeks, in doses up to 800 mg per day given orally. No serious adverse effects were noted with the drug in this large database. Ebrotidine was well tolerated. Ebrotidine, in comparative clinical studies was found to be as effective as ranitidine (Zantac) and in some studies, was shown to have a better ulcer healing property.

Ebrotidine's effect on the physical properties of gastric mucus was evaluated in experimental studies.[12, 13] Ebrotidine was found to change the physicochemical nature of gastric mucus. Mucus gel became thicker with the gel dimension found to be 290 $\mu$m in animals treated with ebrotidine and 223.5 $\mu$m in control. Furthermore, this effect was seen even when ebrotidine was given with indomethacin, a prostaglandin inhibitor known to cause gastric mucosal injury. Ebrotidine evoked a 65% greater increase in hydrophobicity of mucus, a 1.4 fold increase in mucus viscosity and 16% increase in hydrogen ion retardation capacity. Improvements in the mucus gel properties are probably related to ebrotidine's ability to raise the content of mucin and phospholipids in mucus.

[12.] Slomiany, B L, Piotrowski, J and Slomiany, A. Gastroprotective Properties of Ebrotidine. A review. Arzneim-Forsch/Drug Research 1997. 47:459–467.
[13.] Slomiany, B L et al. Enhancement in the protective quality of gastric mucus by ebrotidine during duodenal ulcer healing. Gen. Pharmacol. 1995, 26: 1039–1044.

A concentration dependent increase in sulfomucin secretion was noted with ebrotidine. The sulfomucin elaborated showed a higher content of a high molecular weight mucus glycoprotein form, suggesting that the drug affects the extent of gastric mucin sulfation and its macromolecular assembly. This effect was seen within 3 hours of the administration of the drug directly to the mucosa.

As it is believed that ebrotidine could demonstrate similar effects on cervical mucus, it is believed to be useful during the follicular phase by changing the local mucus quality, rendering it hostile to sperm penetration and potentially providing an effective contraceptive. For ebrotidine and similar agents, systemic dosage is contemplated to a preferred dosage range between 200 to 1600 mg per day. For local application, lower amounts are contemplated with a target of achieving local tissue exposure in the range of 50 to 250 uMol/L.

8. Purinergic Receptors and Purinergic Agents

The second aspect of the invention relates to the development of a new treatment for a bothersome and potentially problematic symptom of menopause, namely vaginal dryness, by stimulating the secretion of cervical mucus and vaginal transudative secretions. The approach outlined here has been successfully utilized to change the mucus quality and increase transudative secretion in the respiratory system, namely, the stimulation of purinergic receptors.

There is a large segment of pre and postmenopausal women who complain of vaginal dryness, although the latter may find vaginal dryness a problem only during the latter part of their menstrual cycles. Vaginal dryness is caused by inadequate mucus secretion and atrophy of the vaginal mucosa, the end result of falling estrogen levels. It is one of the more common side effects of menopause, and leads to quality of life issues along with a propensity for greater incidence of infections. In the absence of estrogens, the vaginal mucosa and the cervical mucosal gland become atrophic. When women are treated with systemic estrogens, there is some relief of symptoms, but even in the presence of estrogen, many women may continue to complain of dryness.

It is a well-known fact that despite data on estrogen's positive effect in menopause, only 20% of women actually take hormones. The remaining 80% may or may not take estrogens and often when they do, they usually stop after a few months. For these women, an alternative or supplementary mode of treating vaginal dryness is needed. It is believed that the present invention may increase mucosal secretion by itself or it may enhance estrogen's actions and may normalize these symptoms in women.

Furthermore, women with breast cancer are often treated with anti-estrogens and vaginal dryness is a debilitating complaint. Estrogen is not used in this population. Another important segment of the population represents younger women undergoing estrogen withdrawal for treating diseases such as endometriosis or even in the late luteal phase of a normal menstrual cycle. These women may actually constitute a unique cohort in which to test the concept. We believe that our application, as discussed below, may indeed help many menopausal women.

Purinergic receptors or receptors responsive to external stimulation by nucleotides such as ATP are now the focus of research in the respiratory and nervous system. In the respiratory system, these agents have been shown to increase the secretions of the respiratory epithelium thereby thinning the mucus. This finding is now being utilized to develop products for cystic fibrosis, a disease characterized by the disabling accumulation of viscid thick inspissated mucus. It has been shown that purinergic stimulation can lead to a thin watery secretion. The novel puringeric stimulants have been identified as part of a discovery effort. This approach can be found in U.S. Pat. Nos. 4,501729, 5,292, 498, and 5,635,160 the entire disclosure of which is incorporated by reference herein.

Other puringeric agents included but not limited to in this invention, are duramycin and related antibiotics, plus other agents that similarly raise the chloride secreting response; dinucleotides and pharmaceutically acceptable salts of Formula I (U.S. Pat. No. 5,635,160), such as $A_2P_4$ stimulating dinucleotides that enhance chloride secretion by increasing transcellular chloride ion transport or alter paracellular permeability, in either case leading to an altered hydration of the overlying or secreted mucus; amiloride and other agents, including but not limited to benzaril and phenamil that similarly hinder sodium ion uptake and lead to altered hydration of mucus; anion secretion inhibitors such as carbonic anhydrase inhibitors [e.g. acetazolamide] and carbamide. Anion secretion inhibitors can find specific use in bacterial vaginosis and like conditions. Furthermore, all of the above products may be used singly or in combination, with or without estrogens, progestogens, androgens and their synthetic and natural derivatives and with or without the mucus secretion/stimulation of hypertonic saline and/or the addition of NaCl.

Agents described above or their antagonists can also increase the secretion and/or enhance the properties of mucus in postmenopausal women, thereby become protective against localized infections and friability and conducive to normal health and normal sexual activity in these women. Similarly they could find use in pre-menopausal women lacking sufficient mucus for proper lubrication. Such products can be given with or without estrogen, progesterone or their synthetic derivatives to enhance or antagonize the effect of a product such as puringeric products. Potentially, these puringeric agents could also stimulate the uterine cervix and the vaginal mucosa. Yet there are signs that the columnar epithelium of the cervix might well show secretory properties similar to pulmonary epithelium as the two share some common. Of particular relevance was the recent demonstration that the paracellular permeability of cultured human cervical epithelium is responsive to local application of nucleotides, thus indicating the presence of puringeric receptors (P2 type) in these cells.[14] It is believed that stimulation of this particular family of receptors can potentially increase transudative fluid and mucus secretion in the menopause, either in the absence or presence of estrogens. An enhancement of mucus secretion by such means would provide welcome relief to women suffering from an inadequacy of vaginal secretions.

[14.] Gorodeski G I and Hopfer U. 1995. Regulation of the paracellular permeability of cultured human cervical epithelium by a nucleotide receptor. J. Soc. Gynecol. Invest. 2:716–20.

Amiloride and other agents that block $Na^+$ uptake, and/or $P_2Y_2$ receptor agonists could be used to enhance cervical mucous secretion, to treat conditions such as dyspareunia and/or infertility. Suchproducts may also potentially, be found to have activity against sexually transmitted diseases. Another use embodied in this invention, are products that can influence puringeric receptors. Although $P_2Y_2$ receptor agonists have been specifically cited, we incorporate by reference the entire classes of purinoceptor subtypes that are selective for nucleotides and agents that mimic the effects of nucleotides. Such an increase in secretion may be helpful in situations such as menopause, when there is much reduced or absent secretion of mucous causing vaginal dryness. This dryness can cause symptoms and signs that are both bothersome to the woman and can cause diseases such as infections. Puringeric receptor products such as but not limited to dinucleotides (U.S. Pat. No. 5,635,160) and uridine triphosphate (U.S. Pat. No. 5,292,498) and the disclosure of the aforesaid two patents are herein incorporated by reference since amiloride itself or other Na+ uptake blockers can enhance the water content of secretions, amiloride (U.S. Pat. No. 4,501,729) is also incorporated by reference.

All of these products may or may not be given with estrogen, progesterone or their synthetic derivatives and all new classes of estrogens and progestogens developed to provide differential effects based on binding to, but not limited to various receptors such as the alpha and beta estrogen receptors and A and B progesterone receptors. These compounds are sometimes called anti-estrogens, anti-progestogens or Selective Estrogen Receptor Modulators, or designer steroid molecules. These compounds can be sometimes associated with vaginal dryness; the current invention may help women who must take these drugs for the menopause or for the treatment or prevention of conditions such as, but not limited to, breast cancer, osteoporosis and cardiovascular disease.

Finally, the dosage of therapeutic agents identified in this application as dinucleotides in suitable formulations for local application can contain active ingredients up to 40% w/w concentration but preferably below 20% w/w concentration. A carrier typically would be a pyrogen free water and/or an aqueous alcohol solution. Powder for insufflation can be placed in a metered dose applicator. In this instance, active agents might range from 0.1 to 100 w/w concentration. Dosing by whatever means would likely fall in the range of 1–20 mg of active agent by weight daily. For local use, nucleotide concentrations can vary between $10^{-3}$ and $10^{-6}$ molar in creams, gels and/or solutions. Amiloride doses are anticipated at 5 mg/day when given systemically and local concentrations of $3\times10^{-2}$ to $3\times10^{-4}$ molar in solutions are anticipated.

Both aspects of the invention can be given orally, systemically, including but not limited to implants and transdermal patches, etc. or given locally, i.e., vaginally, including but not limited to foams, creams, rings, sprays, gels, tablets, films, all manner of solid and liquid dosage forms etc. The products may also be delivered with a variety of devices, including but not limited to tampons, sponges, spray devices, etc. Products insoluble in water such ebrotidine may be formulated after micronization or nanoization in water and a polymer such as carbopol or dissolved in mineral oil and formulated with carbopol.

What is claimed is:

1. A method of affecting the amount of or properties of the cervical and vaginal mucosa comprising administering an effective amount of a composition comprising a compound selected from the group consisting of histamine receptor antagonists and puringeric agents to an individual in need of treatment thereof, wherein the compound alters properties of the mucus selected from the group consisting of rheological properties, hydrogen ion retention, hydrophobicity, changes in phospholipid content, sulfation, glycosylation, macromolecular assembly, surface tension, adhesivity, and transport properties.

2. The method of claim 1 comprising administering to the patient an effective amount of ebrotidine as the histamine receptor antagonist sufficient to achieve a contraceptive effect.

3. The method of claim 1 comprising administering an effective amount of a compound to cause an increase in the viscosity of the cervical mucus in the presence or absence of additional sex steroid hormones.

4. The method of claim 2 wherein ebrotidine is administered at a systemic dosage of ebrotidine of between 200 to 1600 mg per day.

5. The method of claim 2 wherein ebrotidine is administered locally in an amount sufficient to achieve local tissue concentrations of between 50 and 250 micromolar ebrotidine/L.

6. The method of claim 1 wherein the compound is administered orally.

7. The method of claim 1 wherein the compound is administered systemically.

8. The method of claim 1 wherein the compound is administered locally.

9. The method of claim 8 wherein the compound is administered vaginally.

10. The method of claim 8 wherein the compound is formulated by micronization or nanoization.

11. The method of claim 1 wherein the rheological properties are selected from the group consisting of viscosity, elastic modulus, tensile properties, rigidity factors, recoil factors, spinnbarkeit, sperm penetration qualities, consistency, cellularity, and ferning.

12. The method of claim 1 wherein the compound is administered in an amount effective to treat vaginal dryness.

13. The method of claim 1 wherein the compound binds to purinergic receptors or receptors responsive to external stimulation by nucleotides.

14. The method of claim 13 wherein the surinergic agent is selected from the group consisting of duramycin antibiotics, dinucleotides and salts thereof that enhance chloride secretion by increasing transcellular chloride ion transport or alter paracellular permeability, amiloride and other agents that hinder sodium ion uptake and lead to altered hydration of mucus, and anion secretion inhibitors.

15. The method of claim 1 further comprising administering steroidal compounds selected from the group consisting of estrogens, progestogens, and androgens.

16. The method of claim 8 wherein the compound is formulated in a formulation for local administration selected from the group consisting of foams, creams, rings, sprays, gels, tablets, films, tampons, and sponges.

* * * * *